United States Patent [19]

Aizu et al.

[11] Patent Number: 4,848,897
[45] Date of Patent: Jul. 18, 1989

[54] OPHTHALMOLOGICAL DIAGNOSIS APPARATUS

[75] Inventors: Yoshihisa Aizu, Machida; Kouji Ogino; Toshiaki Sugita, both of Hino, all of Japan

[73] Assignee: Kowa Company Ltd., Japan

[21] Appl. No.: 174,840

[22] Filed: Mar. 29, 1988

[30] Foreign Application Priority Data

Mar. 31, 1987 [JP] Japan ............................. 62-75778

[51] Int. Cl.$^4$ .......................... A61B 3/10; A61B 3/14
[52] U.S. Cl. .................................. 351/221; 351/211; 351/206; 128/691
[58] Field of Search ............... 351/206, 211, 221; 128/691, 303.1

[56] References Cited

U.S. PATENT DOCUMENTS 4,423,931  1/1984  Shapiro ........................ 351/211 X Primary Examiner—Rodney B. Bovernick
Attorney, Agent, or Firm—Bruce L. Adams; Van C. Wilks

[57] ABSTRACT

An ophthalmological diagnosis apparatus is disclosed that has an optical spatial frequency filter, a double diffraction optical system whereby an eye fundus image formed at a first image plane that is conjugate with the eye fundus is again formed at a second image plane, a magnifying optical system for expanding the eye fundus image formed on the second image plane, and a detecting aperture for detecting movement of laser speckles formed at the image plane of magnifying optical system as fluctuations in the intensity of the speckle light. Advantages of the apparatus include the ease with which a single, specific blood vessel can be selected; unnecessary light components can be filtered out, improving the S/N ratio of the speckle light detection; the optical system does not need to be high-precision; good operability; and measurement results that are much more reliable and reproducible.

5 Claims, 4 Drawing Sheets

OPHTHALMOLOGICAL DIAGNOSIS APPARATUS

BACKGROUND OF THE INVENTION

1. Field of the Invention

This invention relates to an ophthalmological diagnosis apparatus, and more particularly to an ophthalmological diagnosis apparatus whereby the eye fundus is illuminated by a beam of laser light and the movement of a speckle pattern formed by diffused laser light reflected by the tissue of the fundus at an image plane which is conjugate with the eye fundus is detected as fluctuation in the speckle light intensity to measure the blood flow state for ophthalmological diagnosis.

2. Description of the Prior Art

Conventional methods that employ laser light to measure the state of the blood flow in the eye fundus include those disclosed in Japanese Pat. Laying-open Nos. 55(1980)-75668 and 56(1981)-49134. Both of these are methods for determining blood flow velocity based on the laser Doppler effect, so in each case it is therefore necessary to detect the frequency shift of the laser light caused by the Doppler effect. This can be done using either of two arrangements. One comprises splitting the incident laser beam into two beams forming equal angles with respect to the optical axis of the incident laser beam and directing the split beams into the eye to be examined so that they intersect precisely at the position of the eye fundus blood vessel concerned. The other arrangement is to detect laser light scattered by the eye fundus blood cells from two different directions. In both cases the optical system is complex and needs to be high-precision. In addition, the fact that the angle of beam incidence or light detection has to be known in advance, the fact that a laser beam adjusted to a beam diameter that is substantially equal to the diameter of the blood vessel concerned (which generally measures between several tens and several hundred micrometers) has to be directed onto the blood vessel with high precision, and the fact that the person undergoing examination has to be kept motionless during the period of measurement make these methods extremely difficult to apply clinically and impair the repeatability and reliability of the results thereby obtained.

In order to overcome the aforementioned drawbacks the present inventors have submitted patent applications (Appln. Nos. 61(1986)-38240 and 61(1986)-67339) for a method and apparatus that utilize the laser light speckle phenomenon. According to this method, a laser beam of a prescribed diameter that is larger than the diameter of the blood vessels is used to illuminate the eye fundus so that light scattered and reflected by blood cells in the eye fundus tissue forms a laser speckle pattern. With the plane of the eye fundus defined as the object plane, the movement of the speckle pattern formed at the Fraunhofer diffraction plane with respect to the object plane or at an image plane that is conjugate with respect to the eye fundus is then detected as fluctuations in light intensity by means of finite detecting apertures, and is analyzed to thereby measure the state of blood flow in the eye fundus.

However, with this method, the speckle pattern formed at the Fraunhofer diffraction plane consists of superposed fields of light scattered from all of the scattering points within the region of the fundus illuminated by the laser beam. As such, light scattered from blood cells in the target blood vessel is superposed with light scattered from the blood cells of adjacent blood vessels, making it difficult to evaluate the blood flow in any one specific blood vessel. In addition, light scattered by the walls of blood vessels and surrounding tissue is also included, which forms optical background noise with respect to the light that is scattered by the blood cells in the target blood vessel. This has made it difficult to detect signals having a good S/N (signal/noise) ratio at the Fraunhofer diffraction plane.

SUMMARY OF THE INVENTION

It is therefore an object of the present invention to provide an ophthalmological diagnosis apparatus that is able to detect speckle signals with a good S/N ratio and enable accurate measurement of the state of the blood flow in the eye fundus.

This object of the invention is accomplished by providing an arrangement having an optical spatial frequency filter at a spatial frequency plane, a double diffraction optical system whereby an eye fundus image formed at a first image plane that is conjugate with the eye fundus is reformed at a second image plane, a magnifying optical system for expanding the eye fundus image formed on the second image plane, and a detecting aperture for detecting movement of a laser speckle pattern formed at the image plane of the magnifying optical system as fluctuations in the intensity of the speckle light, whereby opthalmological diagnosis is performed by processing speckle signals obtained by means of the detecting aperture.

In accordance with this arrangement, the image plane is prescribed for detection of the speckle pattern and fluctuations in the intensity of the speckle light at the plane are acquired as signals, enabling the desired blood vessel to be specifically set at the image plane. Thus, in an eye fundus image obtained by means of an eye fundus camera or other such conventional optical systems employing laser light there have been problems such as that unnecessary light reflected or scattered from surrounding tissue becomes conspicuous, and because of the degradation of the image contrast and quality caused by the superposition of such light, the S/N ratio of the output signal becomes insufficient and the image too small for the specified vessel to be selected. In contrast to this, as in accordance with the present invention detection of the speckle light is performed following double diffraction, spatial frequency filtering, and image formation using a microscope optical system, a specific blood vessel can be readily selected, unnecessary light can be excluded, and speckle light can be detected with a good S/N ratio.

Rather than an overall, averaged evaluation of the state of blood flow in a plurality of blood vessels included within the irradiated region of the eye, with respect to the measurement of blood flow in the eye fundus utilizing the speckle phenomenon, this arrangement enables the velocity of the blood flowing through a single specific blood vessel to be measured. In addition, as this arrangement involves none of the restrictively high level of precision that is required of optical systems utilizing the Doppler method, it has good operability and, therefore, yields data having good reproducibility.

BRIEF DESCRIPTION OF THE DRAWINGS

The objects and features of the present invention will become more apparent from the following detailed description in conjunction with the accompanying drawings in which.

DETAILED DESCRIPTION OF THE PREFERRED EMBODIMENTS

Figure 1:
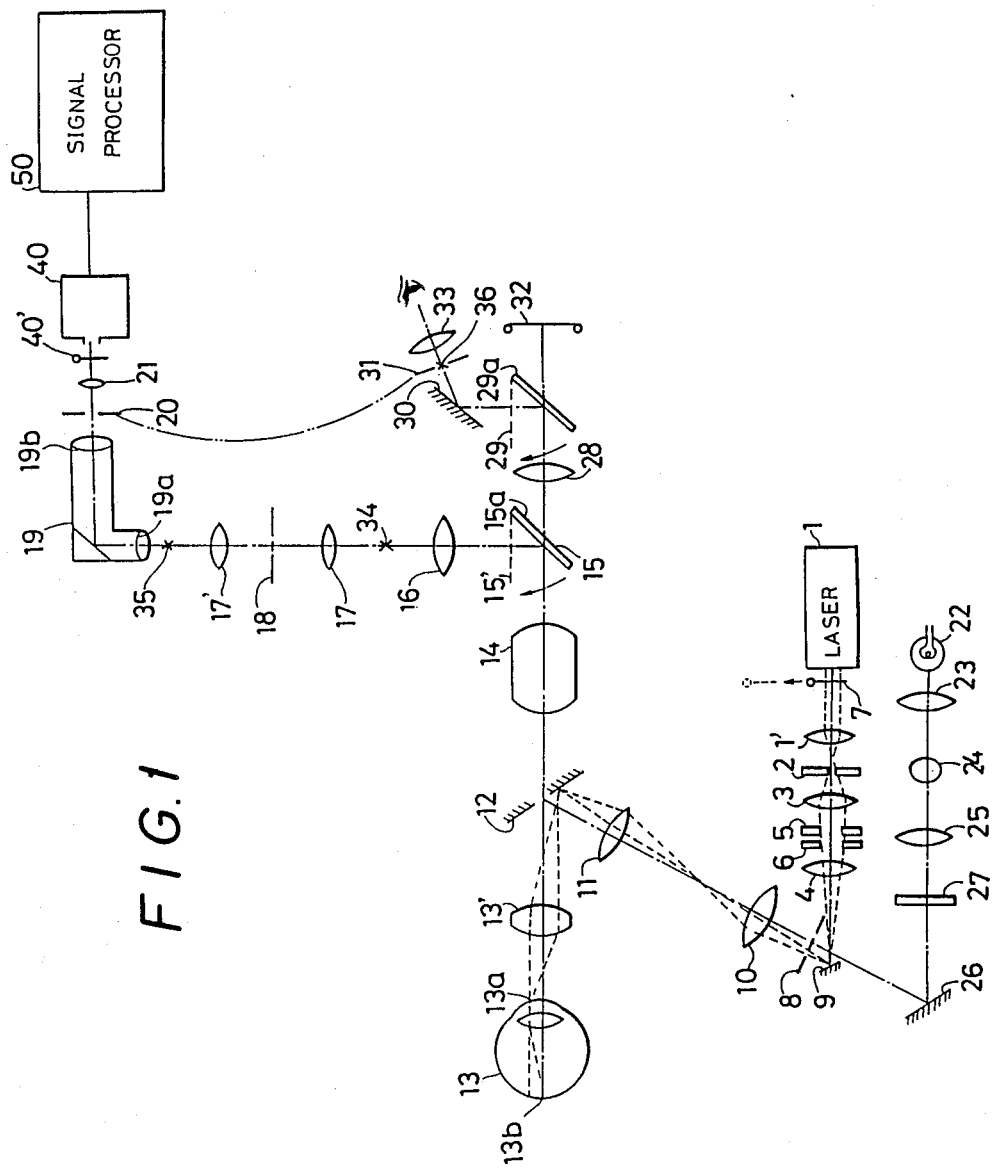
FIG. 1 is a diagram showing the structure of a first embodiment of the apparatus according to the present invention.

The invention will now be described in detail with reference to the embodiments shown in the drawings. The invention is concerned specifically with the fundus region of the eye, and as such the following description relates to when an eye fundus camera is used to measure blood flow in the eye fundus.

Figure 2:
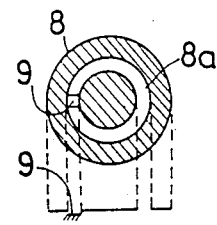
FIG. 2 is a diagram for explaining the structure of a ring slit.

FIG. 1 shows an overall schematic view of an apparatus for carrying out the measurement method according to the present invention. A laser beam such as from a green-light He-Ne (wavelength: 543.5 nm) type laser beam source 1, for example, passes through a condenser lens 1', and then through a light intensity adjustment filter 2 for adjusting the intensity of the beam. Thereafter the beam passes through relay lenses 3 and 4 and is introduced into the eye fundus illuminating optical system of an eye fundus camera. A pair of stops 5 and 6 is disposed between the relay lenses 3 and 4 for selectively adjusting the size and shape of the region of the eye fundus irradiated by the laser beam. Disposed near the beam-emitting end of the laser beam source 1 is a shutter 7 which can be opened or closed as required. As shown in FIG. 2, the laser beam issuing from the relay lens 4 is reflected by a mirror 9 provided in one portion of an annular aperture 8a formed in a ring slit 8 disposed in the eye fundus illuminating optical system, so that the reflected laser beam travels along the same light path leading to the eye fundus under examination as that followed by a beam of light directed onto the eye fundus as illumination for photography and observation.

As a result, the laser beam passes through relay lenses 10 and 11, is reflected by a ring mirror 12, is converged on the cornea 13a of the eye under examination 13 by an objective lens 13' and then diverges as it moves toward the eye fundus 13b which it reaches in a diverged state to thereby form an illuminated region which is larger than the diameter of the blood vessel referred to earlier.

This illuminated area is also illuminated by the illuminating projector of the fundus camera, facilitating observation. The system for providing the illumination for observation is constituted of an observation light source 22, a condenser lens 23, a condenser lens 25, a filter 27 and a mirror 26 disposed on the same light path as a photographic light source 24. As the path of the laser beam coincides with that of the beam of photographic and observation light, the laser beam can be made to impinge on the desired region of the eye fundus 13b by use of the mechanisms for swinging and tilting the eye fundus camera vertically and horizontally and also by use of the eye fixation means.

Figure 3:
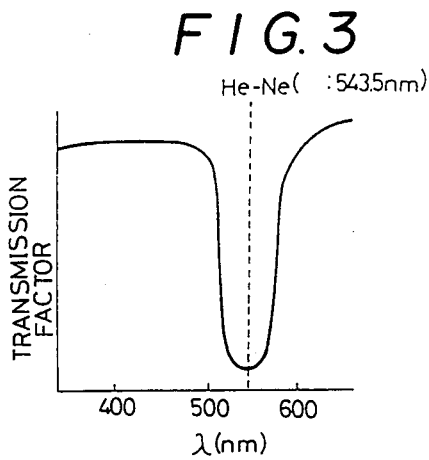
FIG. 3 is a characteristic curve showing the characteristics of a wavelength separation filter used in the embodiment of FIG. 1.

The filter 27 disposed between the condenser lens 25 and the mirror 26 is a wavelength separation filter which, having the type of characteristics shown in FIG. 3, filters out green components from the observation and photographic light.

The speckle light produced when the laser beam is scattered by the blood cells moving in the blood vessels in the eye fundus enters the objective lens 13', passes through the ring mirror 12 and then through a photographic lens 14 to impinge on a wavelength separation mirror 15. Like the filter 27, the wavelength separation mirror 15 exhibits the type of spectral characteristics illustrated in FIG. 3, and since it therefore reflects almost all light components having wavelengths in the green band and passes other light components, it reflects most of the speckle light (green) generated by the He-Ne laser beam. A lens 16 images the reflected light at an image plane 34, and an image is again formed at a plane 35 by a double diffraction system comprised of lenses 17 and 17'. There is a spatial frequency plane between the lenses 17 and 17' at which is disposed a spatial frequency filter 18. The eye fundus image thus filtered and reformed is then magnified by an objective lens 19a and eyepiece lens 19b of a microscope optical system 19. The magnified image passes through a detecting aperture 20, is converged once again by a condenser lens 21 and detected by a photomultiplier 40. A shutter 40' is disposed in front of the photomultiplier 40 and the output signal produced by the photomultiplier 40 and obtained therefrom when this shutter is open is fed into a signal processor 50.

Figure 4:
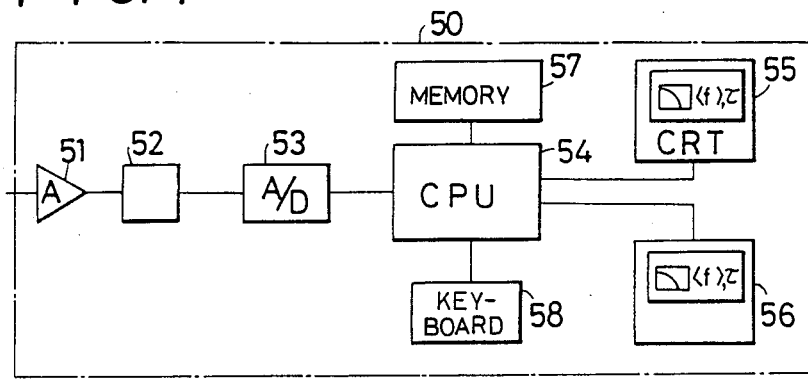
FIGS. 4 and 5 are block diagrams for explaining the structure of different signal processors used in the embodiment of FIG. 1.
Figure 5:
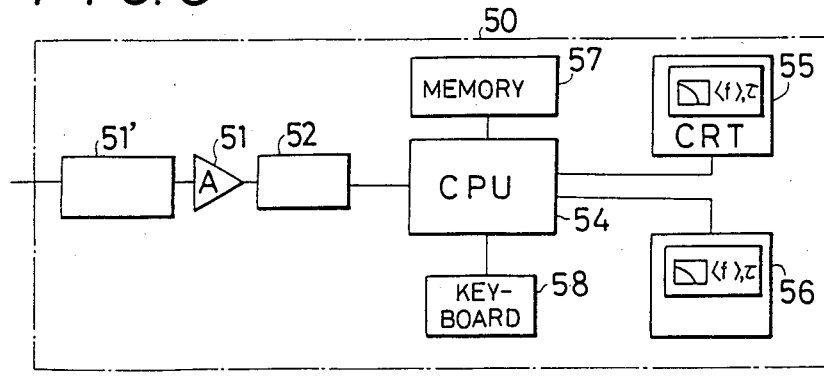

As shown in FIG. 4, the signal processor 50 is constituted of an amplifier 51, a filter 52, an A/D (analog/digital) converter 53, a CPU 54, a CRT display 55, a printer 56, a memory 57 and a keyboard 58. Alternatively, when photon correlation processing is going to be carried out, a photon counting unit 51' is provided in front of the amplifier 51, as shown in FIG. 5.

The light passing through the wavelength separation mirror 15 advances through a relay lens 28, is reflected by a swingable mirror 29 and a mirror 30, and is then directed, via a reticle 31, to an eyepiece 33 through which it can be observed or recorded on a photographic film 32.

With the apparatus arranged as described, after the power has been turned on and the patient positioned, the eye fundus 13b of the eye 13 under examination is observed by means of the observation light optical system constituted by the elements 22 to 26 and the laser light beam source 1 is activated. At this point the filter 2 is used to adjust the light output to the level used for system set-up and the stops 5 and 6 are used to set the size and shape of the region illuminated by the laser beam. Next, the shutter 7 is opened and, after the measurement position has been set, the speckle pattern is confirmed by means of the observation light optical system constituted by the elements 28 to 31.

With respect to this embodiment, to facilitate the illumination with the laser beam, the region of the eye fundus 13b illuminated by the laser beam at the portions at which measurement is to be carried out is set larger than the blood vessel, for example to a diameter of 1 mm to 3 mm. Clearly, then, this can result in the inclusion of a plurality of relatively thick blood vessels in addition to capillaries. When in this case the detection is conducted at the Fraunhofer plane the detected light will consist of superposed rays of light scattered from all the points within the illuminated region. As such, blood flow information obtained from an analysis of the speckle signals will be an averaged evaluation of the state of the blood flow in all the blood vessels falling within the irradiated region. It is because of this that it has been difficult to measure the blood flow in a specific single blood vessel. Moreover, light scattered from the walls of blood vessels and surrounding tissue is also detected, forming optical background noise which degrades the S/N ratio of the speckle signals.

For this reason, in accordance with the method of the present embodiment, detection of the speckle pattern is conducted at a magnified image plane.

That is, a conjugate image of the eye fundus is formed at the image plane 34 shown in FIG. 1. Further, the image is again formed at the plane 35 by the double diffraction system comprised of lenses 17 and 17'. This image is then magnified by the objective lens 19a and eyepiece lens 19b of the microscope optical system 19, and fluctuations in the intensity of the speckle light are detected by the detecting aperture 20 disposed at the plane of the magnified image. The light is then converged by a condenser lens 21 and converted into an electrical signal by the photomultiplier 40, the shutter 40' being in the open position.

The output produced by the photomultiplier 40 during measurement constitutes a speckle signal which varies with time in accordance with the movement of the blood cells. This speckle signal is amplified by an amplifier 51 provided within a signal processor 50, and if necessary it is then passed through a band pass filter 52 the band of which is set so as to remove unnecessary frequency components. As shown in FIG. 4, the signal is then converted into digital form by an A/D converter 53, after which it is subjected to frequency analysis by the execution of a frequency analysis program prepared in advance, and the power spectrum distribution is thereby obtained.

As thus described in the foregoing, as in accordance with this embodiment the detecting aperture 20 is disposed at the magnified image plane, the blood flow in a specific single blood vessel can be measured by selecting the blood vessel image to be measured in the image area of the region illuminated by the laser beam and locating the detecting aperture 20 within the blood vessel image, either by adjusting the position of the detecting aperture 20 or by adjusting the fixation of the eye under examination 13, Therefore, by employing the detection method and signal processing described below, it becomes possible to elucidate the blood flow not as a state but as an absolute velocity value.

Among conventional methods for measuring blood flow velocity as an absolute value in a single specified blood vessel, there is the laser Doppler method mentioned in the above. With this method, the blood vessel concerned is illuminated using laser light tightly focused to form a very fine beam with a diameter substantially equal to or smaller than the diameter of the blood vessel upon which the beam impinges at a predetermined angle, or alternatively, the incident laser beam is split into two beams that are directed so that they intersect at a position within the said blood vessel. The operations required for this are extremely difficult, the optical system complex and the obtained data inconsistent.

Although the embodiment according to the present invention is based on the speckle method, it is very practical because, with respect to relatively large blood vessels, it permits a single specific blood vessel to be selected and the absolute velocity of the blood flow therein to be measured. That is, it enables the absolute velocity of the blood flow in a specific blood vessel to be measured while utilizing the advantages of the speckle method. Because the laser beam is sufficiently larger than the diameter of the blood vessel concerned the vessel does not shift out of the beam, and as the detecting aperture is positioned at a magnified image plane, adjustment is very simple. Moreover, because measurement can be carried out regardless of the angle of beam incidence or angle of light reception and it therefore is not necessary to retrieve the scattered light from a plurality of directions or detect the light at a determined angle, obtaining results that have repeatability and reliability is facilitated. This is a major advantage, compared with the Doppler method.

An embodiment wherein the detecting aperture is located at a magnified image plane will now be described.

Figure 6:
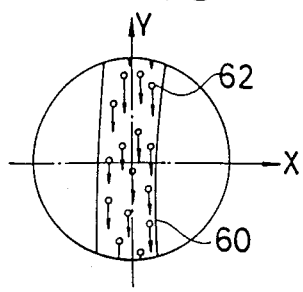
FIG. 6 is a diagram for explaining an eye fundus image that shows image plane speckles and a blood vessel image.
Figure 7:
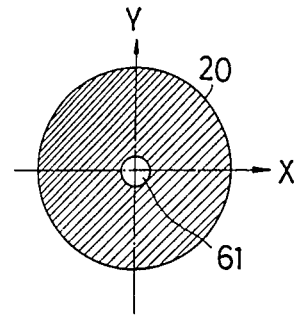
FIG. 7 is an explanatory diagram of a detecting aperture according to one embodiment.

A pinhole, for example, may be utilized as the detecting aperture 20. As an example, when a magnified image of a desired single blood vessel 60 such as shown in FIG. 6 is being observed, if a pinhole such as the pinhole 61 shown in FIG. 7 having a smaller diameter than that of the blood vessel, as observed in the image, is disposed at a portion where the image plane speckles within the vessel are in motion, speckles passing across the detecting aperture 20 will give rise to a corresponding fluctuation in the intensity of the detected light, thereby producing a speckle signal.

Figure 8:
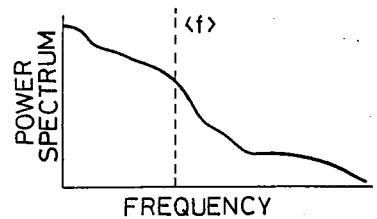
FIG. 8 is a graph for explaining the relationship between frequency and power spectrum.
Figure 9:
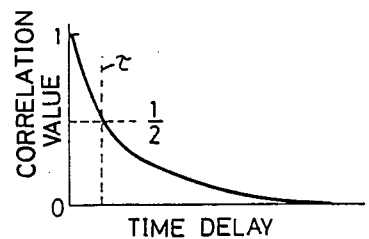
FIG. 9 is a graph for explaining the relationship between time delay and correlation value.

As the rate at which image speckles 62 traverse the aperture changes in proportion to the velocity of the blood flow, an increase in the velocity of the blood flow produces a corresponding increase in the rate at which the speckle signal varies with time, which increases the high frequency component of the signal. After the signal has been subjected to frequency analysis by the signal processor 50 to obtain the power spectrum distribution, the configuration of the power spectrum distribution is evaluated, as shown in FIG. 8, according to mean frequency. Here, there exists a fixed linear relationship between the blood flow velocity and the velocity of the image speckles, and between the velocity of the image speckles and the mean frequency, so that with prior calibration, it is possible to determine the blood flow velocity. This is the same as the case where the signal autocorrelation is obtained with the signal processor 50 and the degree of attenuation evaluated in accordance with the correlation time. If, as shown in FIG. 9, correlation time τ is taken as the time delay for the correlation value to become ½ (or 1/e or the like), the relationship between the inverse thereof 1/τ and image speckle velocity will be linear. In cases where the light scattered from the eye fundus is weak, the signal is processed using the photon correlation method shown in FIG. 5. Comments pertaining to the case illustrated in FIG. 9 can be regarded as applying in precisely the same way in the case of the correlation obtained in this case.

Figure 10:
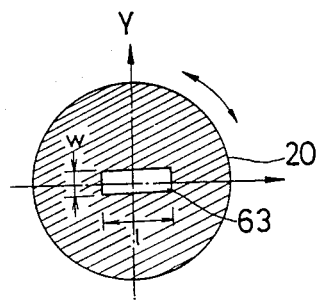
FIG. 10 is an explanatory diagram of a detecting aperture according to another embodiment.

Another example of a detecting aperture 20 that can be employed is that of a slit 63 shown in FIG. 10. With reference to this example, it is generally preferable that the length l of the slit 63 is less than the diameter of the blood vessel on the magnified image plane and that the width ω thereof is less than the length l and as large or larger than the image plane speckle size. Also, the slit is disposed so that its long side is perpendicular to the orientation of the blood vessel, that is, perpendicular to the direction of image plane speckle movement. With this arrangement, the image plane speckle movement within the blood vessel can be detected effectively, and even when there is a distribution of flow velocities within the blood vessel, the velocity can be measured as an average value. In this regard, therefore, the slit configuration has the advantage of providing more consistent data than the pinhole type.

However, because the pinhole 61 is non-directional there is no need to adjust its orientation, but the slit 63 does require to be aligned perpendicularly with respect to the direction of the blood flow in the vessel.

Figure 11A:
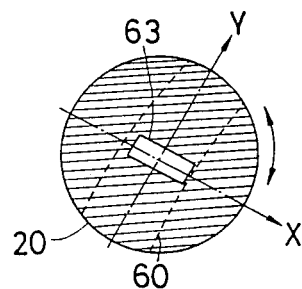
FIG. 11(A) is a diagram for explaining the rotational adjustment capability of a slit aperture.
Figure 11B:
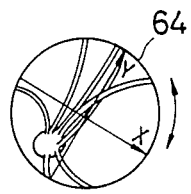
FIG. 11(B) is an explanatory diagram of a reticle.

One way of doing this is to make the slit aperture a rotatably adjustable mechanism that is linked to a reticle 64 constituted of x-axis and y-axis crosshairs, as shown in FIG. 11, and disposed at an image plane 36 formed in front of the eyepiece 33 of the eye fundus camera shown in FIG. 1. One method that can be applied is to use the reticle to bring the y-axis into alignment with the target blood vessel so that the point at which the crosshairs intersect is at the center of the blood vessel, and then to position the slit at the magnified image plane so that it is perpendicular to the direction of the blood flow and, in addition, the center of the slit coincides with the center of the blood vessel.

Figure 12:
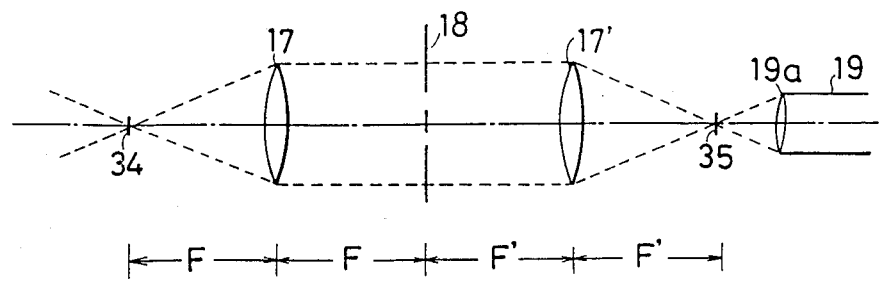
FIG. 12 is a diagram for explaining an arrangement for a double diffraction optical system and spatial frequency filtering.

The double diffraction system and spatial filtering will now be described in more detail. With reference to FIG. 1, at the conjugate plane 34 laser speckle light reflected by the wavelength separation mirror 15 is formed by the lens 16 into an image of the region of the eye fundus illuminated by the laser beam. However, there is still the problem of unnecessary light scattered by the walls of blood vessels and surrounding tissue superposing on the image and making it difficult to achieve good contrast for the observation of speckle movement at the image plane. For this, the type of generally-known double-diffraction and spatial frequency filtering method shown in FIG. 12 is resorted to. Specifically, the lens 17 is positioned so it is separated from the image plane 34 by just a focal distance F which produces a spatial frequency plane at distance F to the rear of the lens 17.

Figures 13A, 13B, 13C:
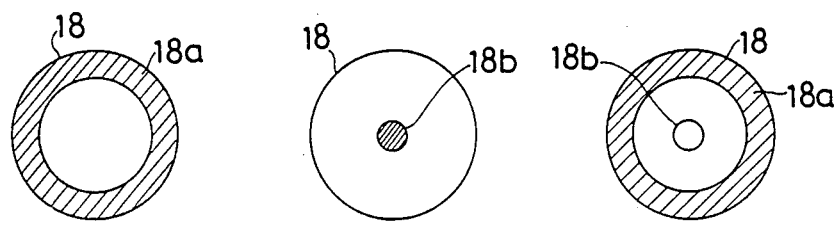
FIGS. 13(A) to 13(C) are explanatory diagrams showing different spatial frequency filtering embodiments.

After the appropriate filtering the image is again formed, via the lens 17' that is positioned a focal distance F' to the rear of the said plane, at a plane that is distance F' to the rear of the lens 17'. Therefore, in contrast to when a single-lens system is used to produce the image, use of a double-diffraction system allows filtering to be done in spatial frequency regions. A low-pass filter constituted of a finite aperture 18a with the optical axis at the center thereof, such as the one illustrated in FIG. 13(A), is used as the spatial frequency filter 18 when the reflected light to be filtered out has a pronounced edgewise bend. To filter out uniform background noise, a high-pass filter with a center optical axis is used constituted of an optical baffle 18b of a predetermined diameter, as shown in FIG. 13(B). The said aperture 18a and baffle 18b can be combined to form the type of band pass filter shown in FIG. 13(C). Which of these is selected depends on the image conditions. Also, the diameters of the aperture 18a and the baffle 18b may be made variable. To detect the moving image speckles with good contrast when the above-mentioned type of spatial frequency filter 18 is employed, it is essential that the light source utilized in the apparatus is a laser light source. The fact that eye fundus cameras were originally intended to be used with the light from an incandescent lamp source and therefore are not able to exclude the powerful reflections from the blood vessel walls and the surrounding tissue produced by laser beam with the high coherency and relatively high intensity shows that the effect of the double diffraction and spatial frequency filter is very considerable.

In FIG. 1, optically, the location of the image formation plane 34 is equivalent to that of the photographic film plane 32. In a conventional fundus camera, the photographic lens 14 are used to adjust the focus as required for each fundus concerned. Even if the lenses 14 are moved by this adjustment, at the film plane 32 the image stays in constant focus. Therefore, an image that is constantly in focus can also be obtained at the image plane 34 that is optically equivalent to the film plane 32, which is effective with respect to the practical utilization of the embodiment illustrated in FIG. 1.

Figure 14:
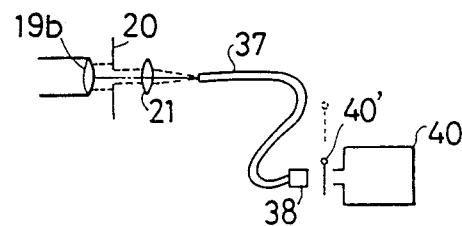
FIG. 14 is a diagram showing the structure of an embodiment that employs an optical fiber from the detecting aperture to a photomultiplier.

The speckle light detected by the detecting aperture 20 and converged by the condenser lens 21, in the embodiment illustrated in FIG. 1, is directed via an optical fiber 37 and a lens 38 into the photomultiplier 40, as illustrated in FIG. 14, where it can be converted into electrical signals. This arrangement makes it possible to separate the photomultiplier 40 from the main unit of the apparatus, which is of practical benefit. This apparatus according to the invention retains the original fundus camera functions, so it is possible to make a photographic record for the purpose of comparison with the results of the blood flow measurements, and monitoring during measurement is also possible.

In the example of this embodiment a green-light He-Ne laser (wavelength: 543.5 nm) is used as the light source. However the method is precisely the same with respect to the use of, for example, a blue-light Ar laser (wavelength: 488.0 nm), or a red-light He-Ne laser (wavelength: 637.8 nm). If the light source wavelength is changed, all that has to be done is to use wavelength separation mirrors 27 and 15 (FIG. 1) with wavelength separation regions that match the wavelength of the light source.

According to the present invention as described in the foregoing, double diffraction and spatial frequency filtering are carried out, an image is formed by means of a optical magnifying system, and a specific blood vessel is then selected for detection and evaluation of speckle signals. This enables the absolute velocity value of the blood flow in a single specific blood vessel to be found. The present invention also facilitates the measurement of the blood flow state with good reproducibility and it has good operability, and as such is highly effective as an ophthalmological diagnosis apparatus. In addition, because the optical system employed does not require the type of precision that is required by methods such as the Doppler method, the apparatus is easy to be realized. Moreover, because the image plane has an ample amount of light for detection purposes, the time required for measurement can be shortened, easing the strain on the person being examined. The apparatus also possesses the original functions of an eye fundus camera, so it has a high clinical utility.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmological diagnosis apparatus wherein an eye fundus is illuminated by a beam of laser light and movement of a laser speckle pattern formed by diffused laser light reflected by the tissue of the fundus at an image plane which is conjugate with the eye fundus is detected as fluctuation in speckle light intensity to conduct ophthalmological diagnosis, comprising:

a laser beam optical system for guiding laser light from a laser beam source, adjusting it to a predetermined beam diameter and causing it to illuminate an eye fundus;

a double diffraction optical system provided with an optical spatial frequency filter at a spatial frequency plane whereby an eye fundus image formed at a first image plane that is conjugate with the eye fundus is reformed at a second image plane;

a magnifying optical system for magnifying the eye fundus image formed at the second image plane;

a detecting aperture means for detecting movement of a laser speckle pattern formed at the image plane of the magnifying optical system as fluctuations in the intensity of the speckle light;

processing means for processing speckle signal obtained with the detecting aperture means;

2. An ophthalmological diagnosis apparatus according to claim 1 wherein said processing apparatus measures blood flow state in tissue of the eye fundus, based on the power spectrum distribution or autocorrelation shape of speckle signals, or based on the shape of photon correlation obtained by photon count processing of speckle signals.

3. An ophthalmological diagnosis apparatus according to claims 1 or 2 wherein said spatial frequency filter is a high-pass filter constituted of a baffle plate of a predetermined diameter, a low-pass filter constituted of a finite aperture of a predetermined diameter, or a bandpass filter constituted of the baffle plate of predetermined diameter concentrically combined with an aperture of predetermined diameter that is larger than that of the said baffle plate.

4. An ophthalmological diagnosis apparatus according to claims 1 or 2 wherein said detecting aperture is a pinhole of a predetermined diameter, or a slit disposed perpendicular to the direction of movement of image plane speckles.

5. An ophthalmological diagnosis apparatus according to claim 4 wherein the detecting slit aperture is made to be rotatable so that it can always remain perpendicular with respect to changes in the direction of movement of image plane speckles.

* * * * *